United States Patent
Raychev et al.

(10) Patent No.: US 10,390,982 B1
(45) Date of Patent: Aug. 27, 2019

(54) SYSTEMS AND METHODS FOR DELIVERY RETRIEVABLE STENTS

(71) Applicant: ICAD ENDOVASCULAR LLC, Fremont, CA (US)

(72) Inventors: Radoslav I. Raychev, Los Angeles, CA (US); Joshua A. Benjamin, Mission Viejo, CA (US); Eric P. Stoppenhagen, Round Rock, TX (US)

(73) Assignee: ICAD ENDOVASCULAR LLC, Fremont, CA (US)

(*) Notice: Subject to any disclaimer, the term of this patent is extended or adjusted under 35 U.S.C. 154(b) by 0 days.

(21) Appl. No.: 16/189,596

(22) Filed: Nov. 13, 2018

(51) Int. Cl.
*A61F 2/962* (2013.01)
*A61F 2/90* (2013.01)
*A61F 2/95* (2013.01)
*A61L 31/16* (2006.01)

(52) U.S. Cl.
CPC ............... *A61F 2/962* (2013.01); *A61F 2/90* (2013.01); *A61F 2002/9522* (2013.01); *A61F 2002/9528* (2013.01); *A61L 31/16* (2013.01)

(58) Field of Classification Search
CPC .... A61F 2/962; A61F 2/90; A61F 2002/9522; A61F 2002/9528; A61F 2002/9505; A61F 2002/9511; A61F 2002/9534; A61F 2/966; A61F 2002/9665
See application file for complete search history.

(56) References Cited

U.S. PATENT DOCUMENTS

| | | | | |
|---|---|---|---|---|
| 5,643,309 | A | * | 7/1997 | Myler ...................... A61F 2/91 606/191 |
| 6,071,286 | A | | 6/2000 | Mawad |
| 6,120,522 | A | | 9/2000 | Vrba et al. |
| 6,468,298 | B1 | * | 10/2002 | Pelton ...................... A61F 2/95 606/194 |
| 6,575,959 | B1 | | 6/2003 | Sarge et al. |
| 7,004,962 | B2 | | 2/2006 | Stinson |
| 7,037,330 | B1 | | 5/2006 | Rivelli et al. |
| 7,294,137 | B2 | | 11/2007 | Rivelli et al. |
| 7,468,070 | B2 | | 12/2008 | Henry et al. |
| 8,092,508 | B2 | | 1/2012 | Leynov et al. |
| 8,197,493 | B2 | | 6/2012 | Ferrera et al. |
| 8,506,615 | B2 | | 8/2013 | Leynov et al. |

(Continued)

FOREIGN PATENT DOCUMENTS

WO 2018169959 A1 9/2018

*Primary Examiner* — Katrina M Stransky
(74) *Attorney, Agent, or Firm* — Stoel Rives LLP

(57) ABSTRACT

Systems and method for delivering and deploying an expandable stent to treat Intracranial atherosclerotic disease (ICAD) involving large and medium-sized blood vessels. The disclosed systems include a catheter, a shaft comprising a distal end disposed within the catheter, an expandable stent comprising a proximal end and a distal end, wherein the shaft is coupled to the expandable stent and the shaft is disposed within the expandable stent, and a plurality of struts, wherein a first end of each strut is coupled to the shaft and a second end of each strut is coupled to the expandable stent. Longitudinal movement of the shaft relative to the expandable stent extends the plurality of struts radially outward and expands the expandable stent, similar to umbrella. The plurality of struts provides radial force to the expandable stent in an expanded configuration to the vessel walls of the patient.

28 Claims, 6 Drawing Sheets

(56) References Cited

U.S. PATENT DOCUMENTS

| | | |
|---|---|---|
| 8,758,364 B2 | 6/2014 | Eckhouse et al. |
| 8,795,317 B2 | 8/2014 | Grandfield et al. |
| 8,864,792 B2 | 10/2014 | Eckhouse et al. |
| 9,005,237 B2 | 4/2015 | Eckhouse et al. |
| 9,034,008 B2 | 5/2015 | Eckhouse et al. |
| 9,561,121 B2 | 2/2017 | Sudin et al. |
| 9,682,216 B2 | 6/2017 | Teitelbaum |
| 9,808,359 B2 | 11/2017 | Ferrera et al. |
| 9,844,381 B2 | 12/2017 | Eckhouse et al. |
| 9,968,360 B2 | 5/2018 | Stoppenhagen et al. |
| 10,022,251 B2 | 7/2018 | Teitelbaum |
| 2003/0144731 A1 | 7/2003 | Wolinksky et al. |
| 2004/0158307 A1 | 8/2004 | Jones et al. |
| 2005/0033410 A1* | 2/2005 | Hogendijk .............. A61F 2/07 623/1.15 |
| 2005/0288763 A1 | 12/2005 | Andreas et al. |
| 2006/0184226 A1 | 8/2006 | Austin |
| 2008/0269868 A1 | 10/2008 | Bei et al. |
| 2010/0331951 A1 | 12/2010 | Bei et al. |
| 2011/0009945 A1 | 1/2011 | Parker et al. |
| 2011/0077731 A1 | 3/2011 | Lee et al. |
| 2011/0152920 A1 | 6/2011 | Eckhouse et al. |
| 2011/0202088 A1 | 8/2011 | Eckhouse et al. |
| 2013/0325055 A1 | 12/2013 | Eckhouse et al. |
| 2013/0325056 A1 | 12/2013 | Eckhouse et al. |
| 2014/0243885 A1 | 8/2014 | Eckhouse et al. |
| 2017/0340330 A1 | 11/2017 | Stoppenhagen |
| 2018/0028209 A1 | 2/2018 | Sudin et al. |
| 2018/0049859 A1 | 2/2018 | Stoppenhagen et al. |
| 2018/0055666 A1 | 3/2018 | Ferrera et al. |

\* cited by examiner

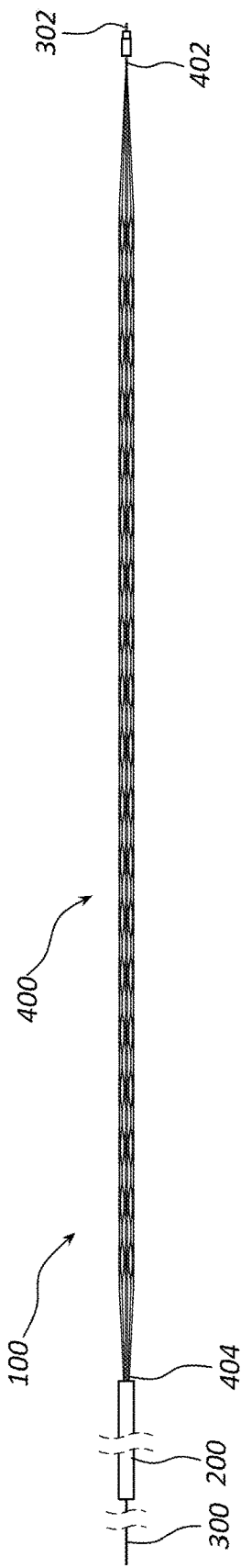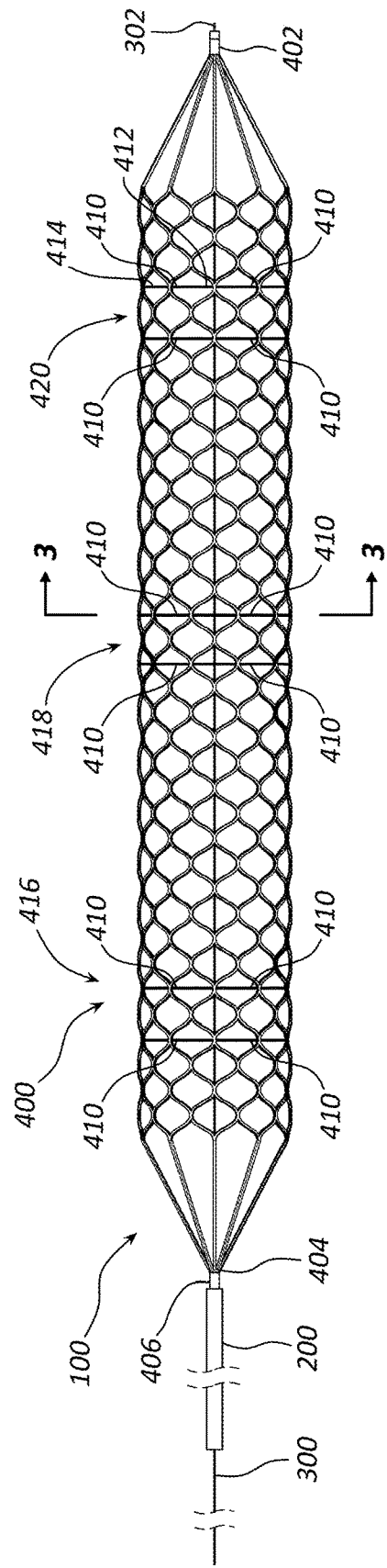

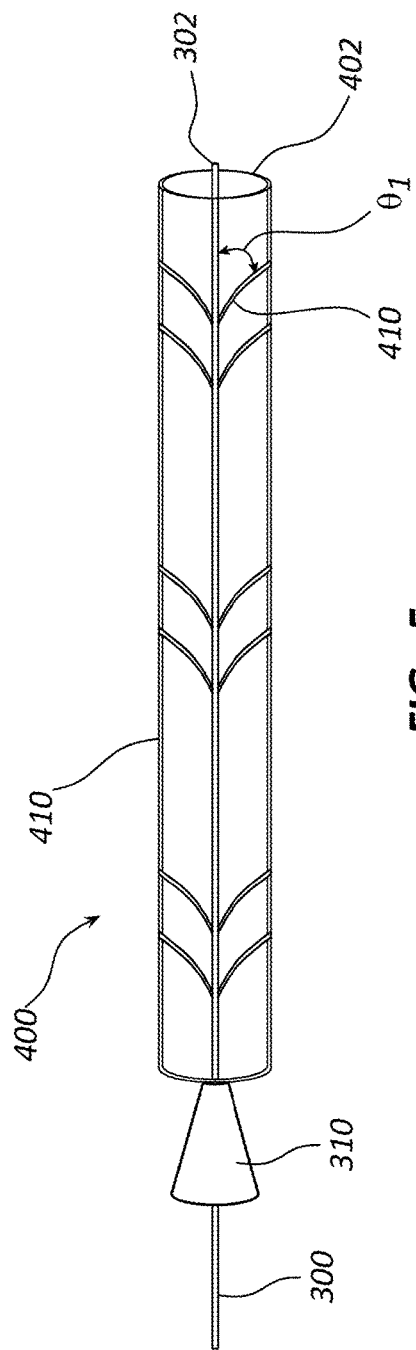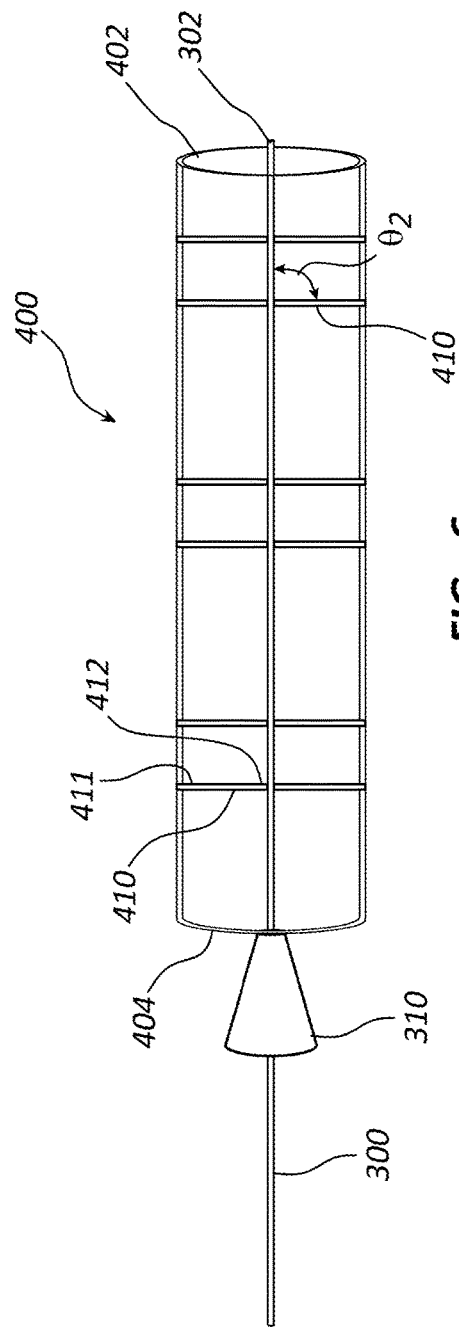

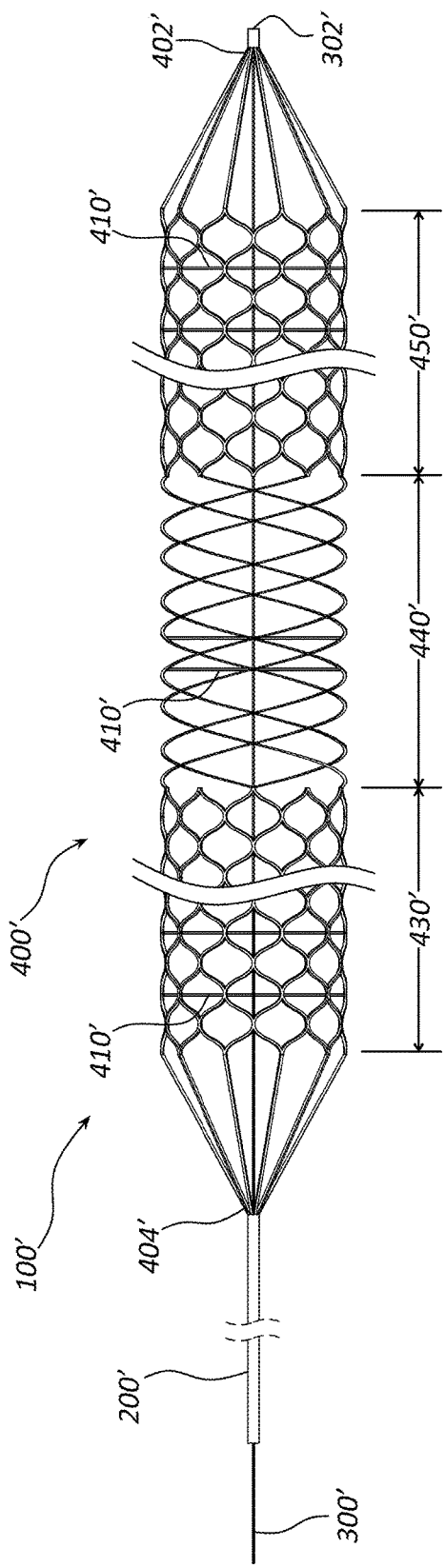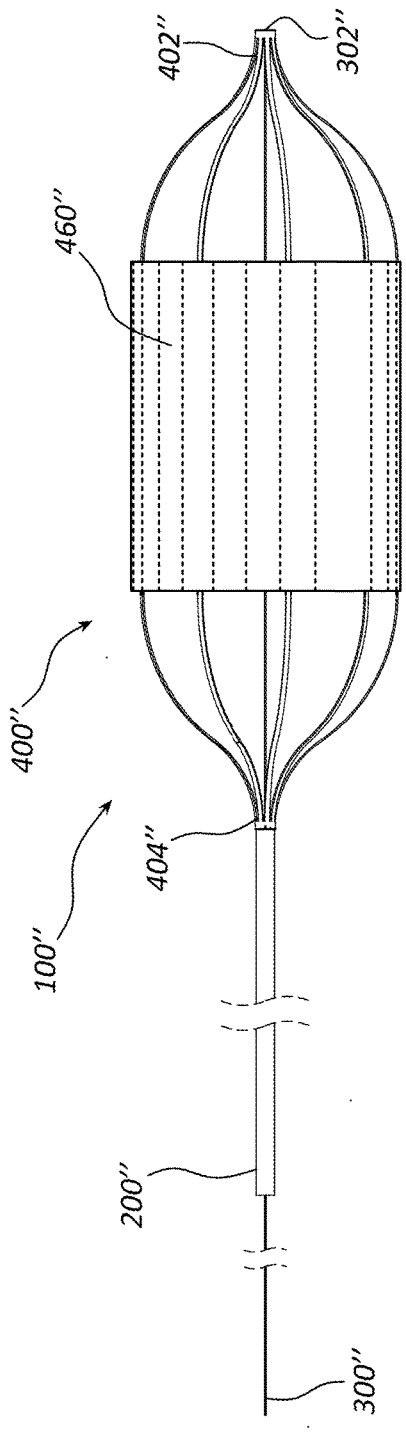

SYSTEMS AND METHODS FOR DELIVERY RETRIEVABLE STENTS

BACKGROUND

The present disclosure relates generally to the field of endovascular treatment of blood vessels. More particularly, some embodiments relate to endovascular treatment of hemodynamically significant intracranial atherosclerotic disease (ICAD).

SUMMARY

Intracranial atherosclerotic disease (ICAD) involving large and medium-sized blood vessels are the leading cause of ischemic stroke worldwide with an estimated occurrence up to 50 percent. It is a predominately prevalent in Asia, South America, and the Middle East and less commonly encountered in Europe and North America. It accounts for 8-10 percent of all ischemic strokes in North America, and 30-50 percent in Asia. The three main mechanisms leading to ischemic stroke due to ICAD are hypoperfusion, branch atheromatous disease, and artery-to-artery embolism.

Current endovascular therapy for ICAD in acute and subacute settings is very limited due to suboptimal current technology, limited ability for balloon angioplasty due to high chance of re-occlusion, and need of permanent stent implantation.

The present disclosure proposes a novel approach to endovascular treatment of hemodynamically significant ICAD, aimed to achieve adequate revascularization without the associate complications of percutaneous angioplasty and stenting. This method and design allow for both temporary and prolonged deployment of retrievable stents with an adjustable radial force. Additionally, there is parent vessel conformability as an attractive alternative to balloon angioplasty and stenting.

BRIEF DESCRIPTION OF THE DRAWINGS

The written disclosure herein describes illustrative embodiments that are non-limiting and non-exhaustive. Reference is made to certain of such illustrative embodiments that are depicted in the figures.

FIG. 1 shows an expandable stent in a collapsed configuration according to one embodiment.

FIG. 2 shows the expandable stent of FIG. 1 in an expanded configuration.

FIG. 5 is a schematic representation of an expandable stent comprising a plurality of struts, according to one embodiment, the expandable stent in a collapsed or semi-collapsed configuration.

FIG. 6 is a schematic representation of the expandable stent of FIG. 5 in an expanded configuration.

FIG. 7 shows an expandable stent in an expanded configuration, the expandable stent comprises a proximal section, a central section, and a distal section, each with a distinct stent design according to one embodiment.

FIG. 8 shows an expandable stent in an expanded configuration, the expandable stent comprises a cover according to one embodiment.

DETAILED DESCRIPTION

Figure 3:
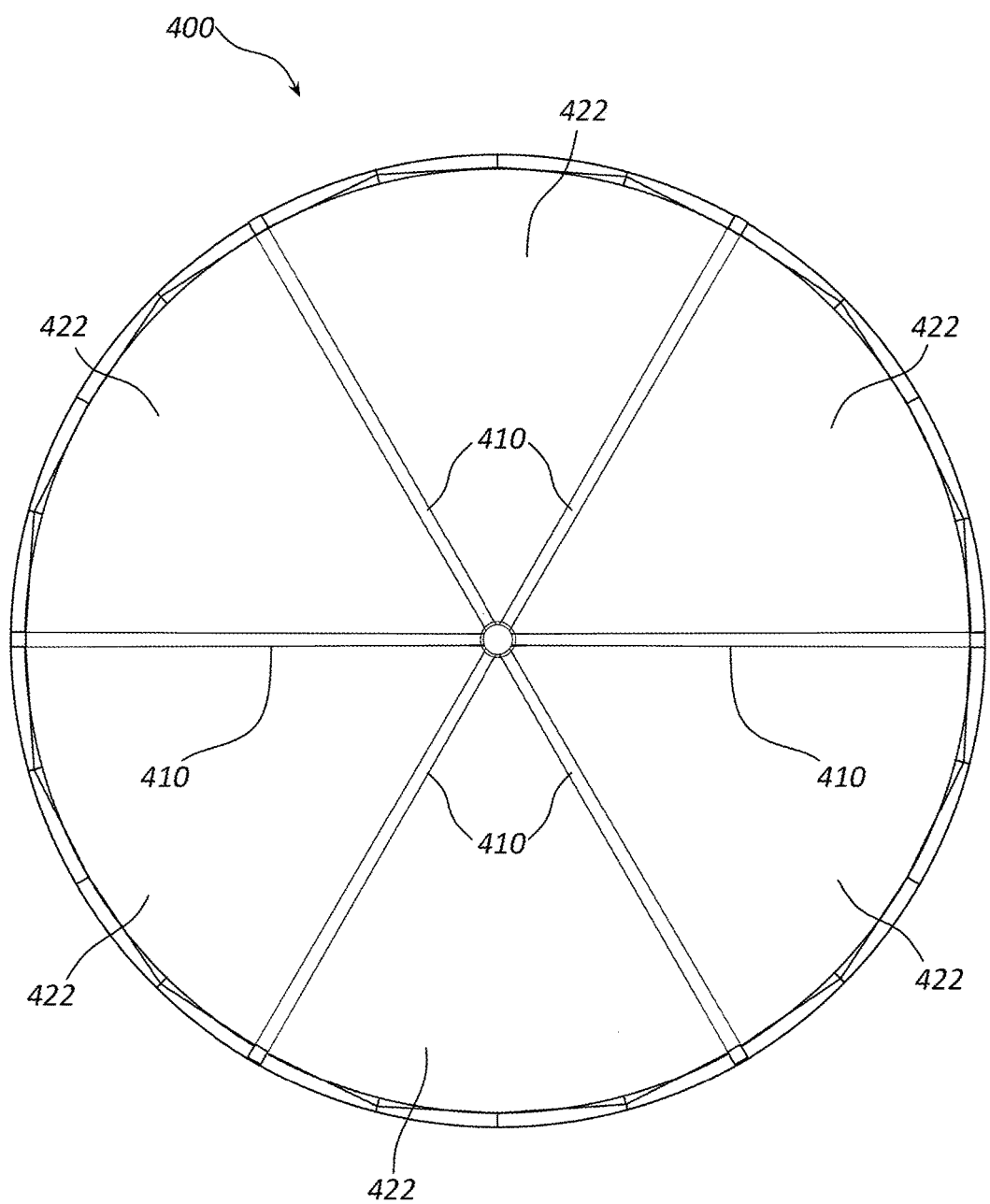
FIG. 3 shows a cross-sectional view of the expandable stent of FIG. 2.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrase "coupled to" is broad enough to refer to any suitable coupling or other form of interaction between two or more entities, including mechanical, fluidic, and thermal interaction. Thus, two components may be coupled to each other even though they are not in direct contact with each other. The phrases "attached to" or "attached directly to" refer to interaction between two or more entities that are in direct contact with each other and/or are separated from each other only by a fastener of any suitable variety (e.g., mounting hardware or an adhesive). The phrase "fluid communication" is used in its ordinary sense, and is broad enough to refer to arrangements in which a fluid (e.g., a gas or a liquid) can flow from one element to another element when the elements are in fluid communication with each other.

The terms "proximal" and "distal" are opposite directional terms. For example, the distal end of a device or component is the end of the component that is furthest from the practitioner during ordinary use. The proximal end refers to the opposite end or the end nearest the practitioner during ordinary use.

FIG. 1 illustrates a retrievable expandable stent delivery system 100 for endovascular treatment of hemodynamically significant intracranial atherosclerotic disease (ICAD). The retrievable expandable stent delivery system 100 includes a catheter 200, a shaft 300, and an expandable stent 400. The shaft 300 and the expandable stent 400 may be disposed within the catheter 200. The catheter 200 may be a microcatheter and have an internal diameter that ranges of 0.017 inches to 0.021 inches. The shaft 300 and the expandable stent 400 may be configured to slidably advance within the catheter 200. In some embodiments, the catheter 200 and the shaft 300 may be coupled to a handle (not shown) that may enable a user to manipulate the catheter 200, the shaft 300, and the expandable stent 400 coupled to the shaft 300.

In some embodiments, the shaft 300 may include an internal lumen. The internal lumen of the shaft 300 may enable the retrievable expandable stent delivery system 100 to be advanced over a guidewire (not shown) that was previously advanced to a target location. The shaft 300 comprises a distal end 302. The distal end 302 of the shaft 300 may have a rounded tip that may help prevent vessel perforation during the procedure.

In some embodiments, the retrievable expandable stent 400 may be coupled to the shaft 300. For example, a distal end 402 of the expandable stent 400 may be coupled to the distal end 302 of the shaft 300. A proximal end 404 of the expandable stent 400 may be coupled to a collar 406 that is configured to encompass the shaft 300. The collar 406 may be configured to slide longitudinally over the shaft 300. In some embodiments, the collar 406 may be locked in a specific location position relative to the shaft 300, enabling the distal end 402 of the expandable stent 400 to move relative to the proximal end 404. The relative movement between the distal end 402 and the proximal end of the expandable stent 400 may be controlled by the handle previously described that may be manipulated by the user.

In some embodiments, the relative movement between the distal end 402 and the proximal end 404 of the expandable stent 400 is configured to expand the expandable stent 400. FIG. 1 illustrates the expandable stent 400 in a collapsed configuration and FIG. 2 illustrates the expandable stent 400 in an expanded configuration. Similarly, the relative movement between the distal end 402 and the proximal end 404 may also collapse the expandable stent 400 after the procedure is completed.

In some embodiments, the expandable stent 400 may be fabricated from a memory material, such as Nitinol, and the expandable stent 400 may be in the collapsed configuration when the expandable stent 400 is sheathed by the catheter 200. The expandable stent 400 may expand when the expandable stent 400 is unsheathed from the catheter 200 enabling the expandable stent 400 to expand to a predetermined shape. Unsheathing may occur by either advancing the expandable stent 400 from the catheter 200 or by retracting the catheter 200 from the expandable stent 400. The expandable stent 400 may be collapsed after the procedure is finished by resheathing the expandable stent 400. Resheathing may occur by retracting the expandable stent 400 back into the catheter 200 or by advancing the catheter 200 over the expandable stent 400.

FIG. 2 illustrates the retrievable expandable stent delivery system 100 with the expandable stent 400 in the expanded configuration. The expandable stent 400 may have a plurality of different design components. The illustrated embodiment of FIG. 2 shows a central region of the expandable stent 400 with a tubular straight shape and a plurality of closed cells.

In some embodiments, the stent may have a tapered configuration. For example, the stent may taper from a proximal end of the stent to a distal end of the stent. In another embodiment, the stent may taper from a distal end to a proximal end of the stent. In another embodiment, the stent may taper in opposite directions from the center of the stent. For example, the stent may taper from the center of the stent to a distal end of the stent and may taper in the opposite direction from the center of the stent to the proximal end of the stent.

In some embodiments, the stent may have a plurality of closed cells rather than a plurality of open cells. In other embodiments, the cells of the stent may be a hybrid cell design that includes a plurality of closed cells and a plurality of open cells. The cell design may be manufactured in a number of methods, such as laser cutting, etc. In some embodiments, the expandable stent 400 may have a braided design.

In some embodiments, an outer surface of the expandable stent 400 may have a porosity that ranges from 10 to 35 percent. In some embodiments, the expandable stent 400 may have a porosity that ranges from 15 to 30 percent.

In the illustrated embodiment of FIG. 2, the expandable stent 400 may further include a plurality of struts 410 that are configured to help expand the expandable stent 400 from the collapsed configuration to the expanded configuration. A first end 412 of each strut 410 may be coupled to the shaft 300 and a second end 414 of each strut 410 may be coupled to the expandable stent 400. Longitudinal movement of the shaft 300 relative to the expandable stent 400 may extend radially outward the plurality of struts 410 and expand the retrievable expandable stent 400 from the collapsed configuration to the expanded configuration. The struts 410 are configured to help maintain the shape of the expandable stent 400 in the expanded configuration.

The plurality of struts 410 may be disposed longitudinally along the shaft 300 between the distal end 402 and the proximal end 404 of the expandable stent 400. The struts 410 may be equally spaced along the shaft 300, or the struts 410 may not be equally spaced along the shaft 300. In some embodiments, the struts 410 may be disposed in subsets along the shaft 300. For example, FIG. 2 illustrates several subsets, a first subset 416 of struts disposed in a proximal portion, a second subset 418 of struts disposed in a central portion, and third subset 420 of struts disposed in a distal portion of the expandable stent 400.

In some embodiments, struts 410 may be radially spaced apart around the shaft 300. This is illustrated in FIG. 3, which is a cross-sectional view of the retrievable expandable stent delivery system 100 taken along cross-sectional line 3-3 shown in FIG. 2. FIG. 3 illustrates a plurality of struts 410 that are radially spaced around the shaft 300. In illustrated embodiments, the struts 410 may be equally spaced around the shaft 300. In other embodiments, the struts 410 may not be equally spaced around the shaft 300. FIG. 3 illustrates six struts 410; however, the present disclosure is not so limited, and there may be more or fewer than six struts. There may be as few as three struts 410 disposed around the shaft 300 and as many as 10 struts disposed around the shaft 300 in a single subset of struts 410.

In some embodiments, the struts 410 that are disposed along the shaft 300 may be radially aligned with the other struts 410 that are disposed along the shaft 300. For example, the first subset 416, the second subset 418, and the third subset 420 may each include a plurality of struts 410 that are disposed around the shaft 300 and are radially aligned with each other. The radial alignment of the struts may create a plurality of channels 422 that extend from the distal end 402 to the proximal end 404 of the expandable stent 400. The channels 422 may enable blood flow or perfusion of blood through the expandable stent 400 in the expanded configuration.

In some embodiments, the longitudinal length of the expandable stent 400 in the expanded configuration may range between 5 mm and 30 mm.

Figure 4:
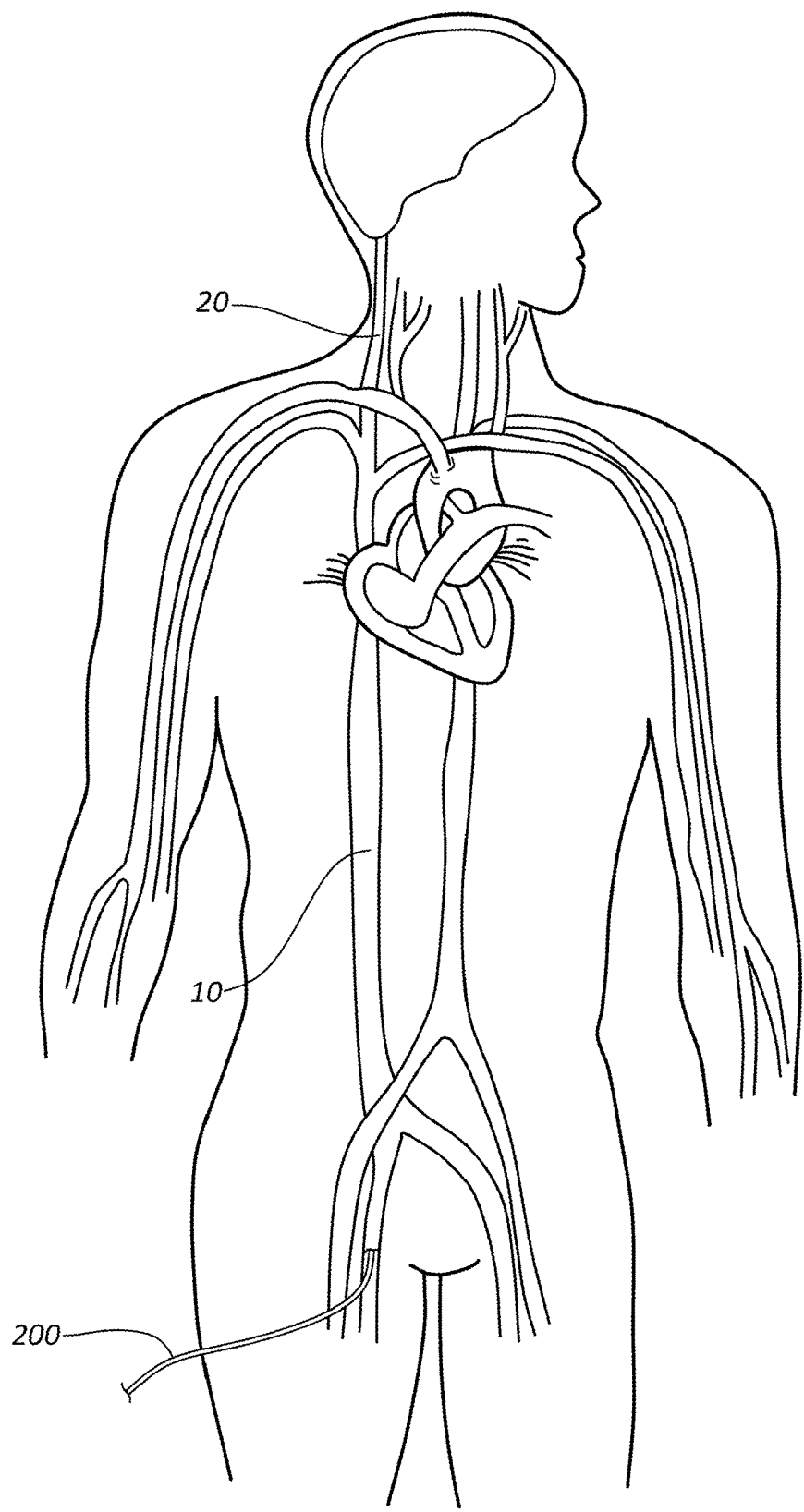
FIG. 4 shows an illustration of an anatomical path of travel of an expandable stent system.

FIG. 4 shows an illustration of an anatomical path of travel of the retrievable expandable stent delivery system 100. The catheter 200 may be inserted into a femoral artery of a patient (using, for example, the Seldinger technique) and advance up through an aorta 10 of the patient, from there the catheter 200 may be advanced up through a carotid artery 20 to an intracranial target location. FIG. 4 illustrates an intracranial target location; however, other vasculature target locations be targeted within the patient's vasculature. The target location may be a partially occluded or fully occluded vessel that may be treated with the retrievable expandable stent delivery system 100. Once the catheter 200 has reached the target location, the shaft 300 and the expandable stent 400 may be advanced out of the catheter 200. The expandable stent 400 may be expanded and the stent may come in contact with plaque disposed on the vessel walls, and the expandable stent 400 may crush or crack the plaque via the adjustable radial force of the expandable stent 400. The expandable stent 400 may be deployed (expanded) at the target location for a prolonged period of time (up to 30 minutes), allowing the vessel patency and distal antegrade flow. The expandable stent 400 may be deployed in blood vessels that have a diameter between 1.5 mm and 7 mm.

In certain embodiments, the expandable stent 400 in the expanded configuration has the ability to maintain vessel patency for 15-30 minutes while the radial force of the expandable stent 400 keeps the plaque from re-coiling, minimizing the elastic recoil and risk of re-occlusion after retrieval of the expandable stent 400. The porosity of the expandable stent 400 minimizes the risk of perforator occlusion and snow-plowing compared to balloons, which cover the plaque uniformly.

In some embodiments, the expandable stent 400 may be detached from the shaft 300 and left in the target area for prolonged treatment. The expandable stent 400 may be detached through a mechanical detachment or electrolytic, thermo mechanical, or other detachment mechanism at a detachment region, which may correspond with the proximal end 404 of the expandable stent 400.

The expandable stent 400 may be radiopaque or may comprise a plurality of radiopaque markers that may enable a user or medical professional to see the retrievable expandable stent delivery system 100 using medical imaging.

FIGS. 5 and 6 are schematic representations of the deployment and expansion of the expandable stent 400. The expandable stent 400 opens radially like an umbrella. FIG. 5 illustrates the expandable stent 400 in the collapsed or semi-collapsed configuration. In the collapsed or semi-collapsed configuration, the struts 410 are angled relative to the shaft 300 at an angle $\theta_1$. In some embodiments, the angle $\theta_1$ may range between 0 and 15 degrees in the collapsed configuration. In some embodiments, the angle $\theta_1$ may range between 0 and 75 degrees in the semi-collapsed configuration FIG. 5 illustrates the struts 410 oriented in a distal direction. Reseathing of the stent may be facilitated when the plurality of struts are oriented in the distal direction. In some embodiments, the struts 410 may be oriented in a proximal direction.

A user may expand the expandable stent 400 to the expanded configuration, as illustrated in FIG. 6, by extending the plurality of struts 410 radially outward, which expands the expandable stent 400. In the expanded configuration, the struts 410 may be angled relative to the shaft 300 at an angle $\theta_2$. In some embodiments, the angle $\theta_2$ may range between 45 and 90 degrees. In some embodiments, the angle $\theta_2$ may range between 75 and 90 degrees. The angle $\theta_2$ determines that amount of radial force that is applied to the expandable stent 400 in the expanded configuration. The closer the angle $\theta_2$ is to 90 degrees the more radial force the struts 410 apply to the expandable stent 400. This enables a user to apply an adjustable radial force to the outer surface of the expandable stent 400 that changes relative to the angle of the struts relative to the shaft 300. For example, the smaller the angle the smaller the radial force and the larger the angle the large the radial force up to 90 degrees. Accordingly, the user may control the amount of radial force applied to the vessel walls of a patient by controlling the movement of the shaft 300 and the radial outward movement of the plurality of struts 410. The struts 410 may apply between 0.00590 and 0.0090 Newtons/mm of radial force.

As discussed previously, the distal end 302 of the shaft 300 may be coupled to the distal end 402 of the expandable stent 400. The shaft 300 may comprise a locking mechanism 310 that is configured to prevent movement of the proximal end 404 of the expandable stent 400 relative to the shaft 300. The locking mechanism may be achieved via a handle locking the shaft 300 relative to the catheter 300.

The expandable stent 400 may be expanded from the collapsed configuration to the expanded configuration by moving the distal end 402 of the expandable stent 400 toward the proximal end 404 of the expandable stent 400. This may be accomplished by engaging the locking mechanism 310 and preventing movement of the distal end 402 of the expandable stent 400. Similarly, the expandable stent 400 may be collapsed from the expanded configuration to the collapsed configuration by moving the distal end 402 of the expandable stent 400 away from the proximal end 404 of the expandable stent 400.

The expandable stent 400 may be expanded by applying a proximally oriented force (pulling) to the shaft 300. The distal end 302 of the shaft 300 is coupled to the distal end 402 of the expandable stent 400 and the distal end 402 of the expandable stent 400 is pulled toward the proximal end 404 of the expandable stent 400. The proximal end 404 of the expandable stent 400 is locked in position via the locking mechanism 310 and prevents movement of the proximal end 404 when the proximally oriented force is applied to the shaft 300. The reverse movement would collapse the expandable stent 400 from the expanded configuration to the collapsed configuration.

As illustrated in FIG. 5, the expandable stent 400 may also be expanded by applying a distally oriented force (pushing) to the expandable stent 400. In this configuration, the distal end 302 of the shaft 300 and the distal end 402 of the expandable stent 400 are coupled together. The expandable stent 400 may be coupled to an outer shaft that encompasses the shaft 300 and a user may apply the distally oriented force to the outer shaft to move the proximal end 404 of the expandable stent 400 toward the distal end 402 of the expandable stent 400.

FIG. 7 depicts an embodiment of a retrievable expandable stent delivery system 100' that resembles the retrievable expandable stent delivery system 100 described above in certain respects. Accordingly, like features are designated with like reference numerals with apostrophes added. For example, the embodiment depicted in FIG. 7 includes a shaft 300' that may, in some respects, resemble the shaft 300 of FIGS. 1-3 and 5-6. Relevant disclosure set forth above regarding similarly identified features thus may not be repeated hereafter. Moreover, specific features of the retrievable expandable stent delivery system 100 and related components shown in FIGS. 1-3 and 5-6 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the retrievable expandable stent delivery system 100' and related components depicted in FIG. 7. Any suitable combination of the features, and variations of the same, described with respect to the retrievable expandable stent delivery system 100 and related components illustrated in FIGS. 1-3 and 5-6 can be employed with the retrievable expandable stent delivery system 100' and related components of FIG. 7, and vice versa. This pattern of disclosure applies equally to further embodiments depicted in subsequent figures and described hereafter, wherein the apostrophes may be further incremented.

FIG. 7 illustrates a retrievable expandable stent delivery system 100' that comprises a catheter 200', a shaft 300', and an expandable stent 400'. The expandable stent 400' may include a proximal portion 430', a central portion 440', and a distal portion 450'. Each portion may have a distinct design configuration. For example, the proximal portion 430' and the distal portion 450' comprises a plurality of closed cells. The central portion 440' may include a helical section that comprises a plurality of helical wires that rotate around the shaft 300'. The helical section may provide additional flexibility for the expandable stent 400' to help enable the expandable stent 400' conform or adapt to the blood vessel curvature without too much vessel straightening effect and minimal plaque or vessel injury.

FIG. 8 illustrates a retrievable expandable stent delivery system 100" that comprises a catheter 200", a shaft 300", and an expandable stent 400". The expandable stent 400" may comprise a porous cover 460". The cover 460" may be fine braided mesh, electrospun PTFE, laser cut urethane, porous nitinol thin film, or other suitable materials.

In some embodiments, the cover 460" may have a hydrophilic surface that helps minimize thrombogenicity. In some embodiments, the expandable stent 400" may have a hydrophilic surface, such as a hydrophilic coating that helps minimize thrombogenicity.

Figure 9:
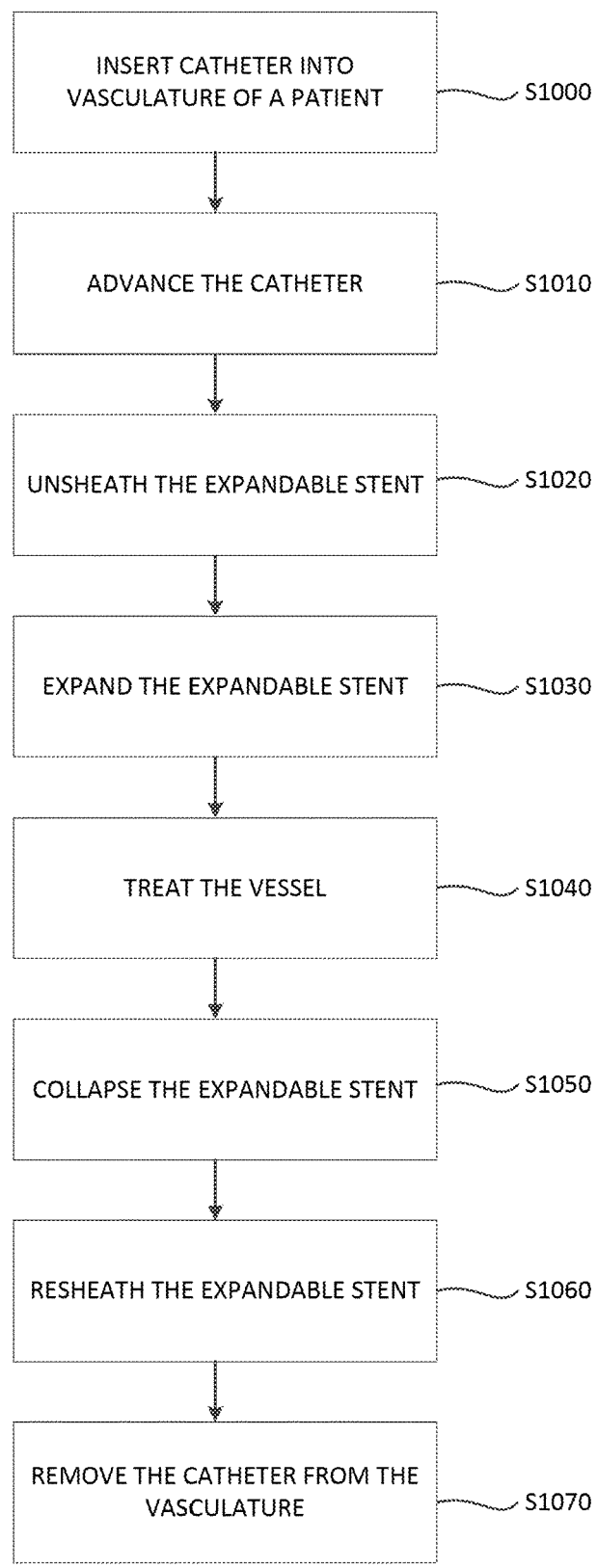
FIG. 9 shows a method of deploying an expandable stent in a patient's vasculature according to one embodiment.

FIG. 9 shows a method of deploying the expandable stent 400 in the vasculature of a patient. Step S1000 describes inserting the catheter 200 into the vasculature of the patient. As previously discussed, the catheter 200 may be inserted into a femoral artery of the patient (using, for example, the Seldinger technique). The catheter 200, however, may be inserted into various different locations of the patient's vasculature. Step S1010 describes advancing the expandable catheter 200 to a target location. FIG. 4 illustrates advancing up through the aorta 10 of the patient; from there the catheter 200 may be advanced up through a carotid artery 20 to an intracranial target location. Other vasculature target locations are within the scope of these disclosure and be anywhere within the patient's vasculature.

Step S1020 describes unsheathing the expandable stent 400 from the catheter 200. This may be accomplished by advancing the expandable stent 400 out of the catheter 200 or by retracting the catheter 200 from the expandable stent 400.

Step S1030 describes expanding the expandable stent 400. As previously described, the expandable stent 400 may expand because it is fabricated from a memory material, such as Nitinol, or the expandable stent 400 may expand via relative movement of the distal end 402 of the expandable stent 400 toward the proximal end 404 of the expandable stent 400. This movement may occur by an umbrella-like movement, by pulling the shaft 300 and extending the plurality of struts 410 radially outward to expand the expandable stent 400.

Step S1040 describes treating the vessel in the target location of the patient. Treatment relies on expanding the expandable stent 400 and crushing or cracking the plaque in the target location. The struts 410 provide an adjustable radial force to crack or crush the plaque and to maintain the shape of the expandable stent 400. The amount of radial force applied by the expandable stent is adjustable and may be controlled by the user. As previously discussed, the relative angle of the plurality of struts 410 relative to the shaft 300 determines the amount of force applied by the outer surface of the expandable stent 400. The smaller the angle the smaller the radial force and the larger the angle the higher the radial force up to 90 degrees. Treatment of the vessel may occur for a predetermined amount of time (up to 30 minutes) or the expandable stent 400 may be detached from the shaft 300 and left in place for a prolonged period to be possibly retrieved later.

Step S1050 describes collapsing the expandable stent 400 to its collapsed configuration after the treatment has been performed. Once the expandable stent 400 is in its collapsed configuration, the expandable stent 400 may be resheathed as described in step S1060. The expandable stent 400 may be resheathed by retracing the expandable stent 400 within the catheter 200 or by advancing the catheter 200 over the expandable stent 400.

Step 1070 describes removing the catheter 200 from the patient's vasculature after the treatment of the vessel has been completed.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

The invention claimed is:

1. A stent delivery system for delivery and deploying an expandable stent comprising:
   a catheter;
   a shaft comprising a distal end, disposed within the catheter;
   an expandable stent comprising a proximal end and a distal end, wherein the shaft is attached directly to the expandable stent and the shaft is disposed within the expandable stent; and
   a plurality of struts disposed within the expandable stent, wherein a first end of each strut is coupled to the shaft and a second end of each strut is coupled to the expandable stent, wherein longitudinal movement of the shaft relative to the expandable stent pulls the distal end of the expandable stent and the proximal end of the expandable stent toward one another, extends the plurality of struts radially outward, and expands the expandable stent, and wherein the plurality of struts provide an adjustable outward radial force to an outer surface of the expandable stent.

2. The stent delivery system of claim 1, wherein the distal end of the shaft is coupled to the distal end of the expandable stent.

3. The stent delivery system of claim 1, wherein a distally oriented force applied to the shaft extends the plurality of struts radially outward, expanding the expandable stent.

4. The stent delivery system of claim 1, wherein a proximally oriented force applied to the expandable stent extends the plurality of struts radially outward, expanding the expandable stent to an expanded configuration.

5. The stent delivery system of claim 1, wherein the struts are disposed at the distal end of the expandable stent and the struts are disposed at a proximal end of the expandable stent to an expanded configuration.

6. The stent delivery system of claim 1, wherein the plurality of struts are disposed longitudinally along the expandable stent and the plurality of struts are radially aligned with each other, and wherein in an expanded configuration, radial alignment of the plurality of struts creates a plurality of channels that extend a length of the expandable stent.

7. The stent delivery system of claim 1, wherein the plurality of struts comprise subsets of struts, wherein a first subset of struts are coupled to a predetermined position of the shaft and are radially spaced apart from each other and a second subset of struts are coupled to a predetermined position of the shaft distal to the first subset of struts and are radially spaced apart from each other, and wherein the first subset of struts and the second subset of struts are radially aligned.

8. The stent delivery system of claim 1, wherein the expandable stent in an expanded configuration provides a radial force that ranges between 0.00590 and 0.0090 Newtons/mm.

9. The stent delivery system of claim 1, wherein in a collapsed configuration, the plurality of struts is oriented in a distal direction.

10. The stent delivery system of claim 1, wherein in an expanded configuration, the plurality of struts is oriented in a proximal direction.

11. The stent delivery system of claim 1, wherein the shaft comprises a locking mechanism, wherein the locking mechanism is configured to lock the position of the proximal end of the expandable stent relative to the distal end of the expandable stent.

12. The stent delivery system of claim 1, wherein the expandable stent comprises a porosity that ranges from 10 to 35 percent.

13. The stent delivery system of claim 1, wherein the expandable stent comprises a porosity that ranges from 15 to 30 percent.

14. The stent delivery system of claim 1, wherein the expandable stent comprises a cover.

15. The stent delivery system of claim 1, wherein the expandable stent comprises a proximal portion, a central portion, and a distal portion, wherein the central portion comprises a plurality a helical wires that rotate around the shaft.

16. An expandable stent system comprising:
a shaft comprising a distal end;
an expandable stent comprising a proximal end and a distal end, wherein the shaft is attached directly to the expandable stent and the shaft is disposed within the expandable stent; and
a plurality of struts disposed within the expandable stent, wherein a first end of each strut is coupled to the shaft and a second end of each strut is coupled to the expandable stent,
wherein the plurality of struts extends radially outward and expands the expandable stent to an expanded configuration, and
wherein the plurality of struts radially outward movement is configured to provide an adjustable outward radial force to an outer surface of the expandable stent.

17. The expandable stent system of claim 16, wherein longitudinal movement of the shaft relative to the expandable stent extends the plurality of struts radially outward.

18. The expandable stent system of claim 16, wherein the expandable stent in an expanded configuration provides a radial force that ranges between 0.00590 and 0.0090 Newtons/mm.

19. A method for deploying a retrievable expandable stent comprising:
inserting a catheter into a vasculature of a patient, wherein an expandable stent system is disposed within the catheter, the expandable stent system comprising:
a shaft comprising a distal end;
an expandable stent comprising a proximal end and a distal end, wherein the shaft is attached directly to the expandable stent and the shaft is disposed within the expandable stent; and
a plurality of struts disposed within the expandable stent, wherein a first end of each strut is coupled to the shaft and a second end of each strut is coupled to the expandable stent,
advancing the catheter to a target location within the patient;
deploying the expandable stent outside a distal end of the catheter; and
selectively controlling an outward radial force and size of the expandable stent to expand the expandable stent against vessel walls, wherein longitudinal movement of the shaft relative to the expandable stent extends the plurality of struts radially outward and expands the expandable stent.

20. The method of claim 19, wherein the expandable stent is deployed in an expanded configuration against the vessel walls for up to 30 minutes before collapsing the expandable stent to a collapsed configuration.

21. The method of claim 19, wherein deploying the expandable stent comprises deploying the expandable stent into an intracranial target location to treat the patient for intracranial atherosclerotic disease (ICAD).

22. The method of claim 21, wherein advancing the catheter to the target location comprises advancing the catheter through a femoral artery, aorta, and carotid artery of the patient to the intracranial target location.

23. The method of claim 21, wherein controlling the outward radial force and size of the expandable stent comprises expanding the expandable stent to come in contact with plaque disposed on the vessel walls, and adjusting the outward radial force to crush or crack the plaque with the expandable stent.

24. The method of claim 23, further comprising maintaining the outward radial force while allowing blood flow through the expandable stent.

25. The method of claim 19, wherein deploying the expandable stent comprises deploying the expandable stent in a blood vessel having a diameter between 1.5 millimeters (mm) and 7 mm.

26. The method of claim 25, wherein selectively controlling the outward radial force comprises selectively applying between 0.00590 and 0.0090 Newtons/mm of outward radial force.

27. The method of claim 19, wherein selectively controlling the outward radial force and size of the expandable stent comprises:

moving the distal end of the expandable stent and the proximal end of the expandable stent toward one another; and engaging a locking mechanism to prevent movement of the distal end of the expandable stent and the proximal end of the expandable stent relative to one another.

28. The method of claim 19, further comprising using the plurality of struts to provide an inward radial force to the expandable stent to collapse the expandable stent for removal through the catheter.

\* \* \* \* \*